United States Patent [19]
Takahashi et al.

[11] Patent Number: 5,602,326
[45] Date of Patent: Feb. 11, 1997

[54] APPARATUS AND METHOD FOR MEASURING CONCENTRATIONS OF GAS COMPONENTS

[75] Inventors: Tomonori Takahashi, Chita; Toshihiro Yoshida, Nagoya; Takao Murase, Konan; Nobuhide Kato, Ama-gun; Yuji Katsuda, Nagoya, all of Japan

[73] Assignee: NGK Insulators, Ltd., Japan

[21] Appl. No.: 546,542

[22] Filed: Oct. 20, 1995

[30] Foreign Application Priority Data

Oct. 24, 1994 [JP] Japan .................. 6-258109

[51] Int. Cl.$^6$ .................................. G01N 7/00
[52] U.S. Cl. .................. 73/31.06; 73/23.31
[58] Field of Search .................. 73/23.31, 31.05, 73/31.06

[56] References Cited

U.S. PATENT DOCUMENTS

| | | | |
|---|---|---|---|
| 2,965,842 | 12/1960 | Jacobson | 73/31.06 |
| 3,932,807 | 1/1976 | Wilson | 334/71 |
| 5,217,692 | 6/1993 | Rump et al. | 422/98 |
| 5,460,711 | 10/1995 | Riegel et al. | 204/425 |
| 5,476,001 | 12/1995 | Hoetzel et al. | 73/23.31 |
| 5,505,837 | 4/1996 | Friese et al. | 204/425 |

FOREIGN PATENT DOCUMENTS

| | | | |
|---|---|---|---|
| 45-17038 | 6/1970 | Japan . | |
| 63-313047 | 12/1988 | Japan | G01N 27/12 |
| 1-150849 | 6/1989 | Japan | G01N 27/12 |

Primary Examiner—Robert Raevis
Assistant Examiner—Jay L. Politzer
Attorney, Agent, or Firm—Parkhurst, Wendel & Burr, L.L.P.

[57] ABSTRACT

A metal oxide semiconductor element is arranged in a measuring chamber in which an atmosphere is introduced. A resistance of the metal oxide semiconductor element is varied corresponding to a concentration of a specific gas component. An oxygen pump, having a solid-electrolyte element with an oxygen ion transmitting property and a pair of electrodes arranged on both sides of the solid-electrolyte element, is provided. One electrode of the oxygen pump is arranged in the measuring chamber. The measuring chamber is communicated with the atmosphere through a hole as a gas diffusion resistant means. A resistance of the metal oxide semiconductor element is measured when the metal oxide semiconductor element is exposed in the atmosphere so as to obtain a concentration of a specific gas component, while an oxygen partial pressure in the measuring chamber is controlled by the oxygen pump.

6 Claims, 6 Drawing Sheets

FIG_4

FIG_5

FIG. 6

FIG_7

FIG_8

5,602,326

APPARATUS AND METHOD FOR MEASURING CONCENTRATIONS OF GAS COMPONENTS

BACKGROUND OF THE INVENTION (1) Field of the Invention

The present invention relates to an apparatus and a method for measuring concentrations of gas components, which can measure concentrations of specific gas components even in a gas in which an oxygen partial pressure is varied.

(2) Related Art Statement

If a metal oxide semiconductor (MOS) is disposed in an atmosphere or a gas including various specific gas components, a resistance of the MOS varies. Prior methods for measuring concentrations of specific gas components have used the resistance variation mentioned above. In the method mentioned above, gas components such as CO, $CO_2$, NO, $NO_2$, $H_2$, $H_2O$, $SO_2$, HCl, $H_2S$ and so on can be measured.

For example, in Japanese Patent Laid-open Publication No. 63-313047 (JP-A-63-313047), $SnO_2$ is used as the MOS, and a concentration of $H_2S$ is measured. In Japanese Patent Laid-open Publication No. 1-150849 (JP-A-1-150849), $TiO_2$ is used as the MOS, and a concentration of NO is measured. In Japanese Patent Publication No. 45-117038 (JP-B-45-17038), $WO_3$ is used as the MOS, and a concentration of $NH_3$ is measured. In all the cases mentioned above, a concentration of the gas component is determined by detecting a resistance of the MOS in response to a variation of the specific gas concentration, and comparing the resistance thus detected with a predetermined reference curve showing a relation between a resistance and a gas concentration of the MOS.

Figure 4:
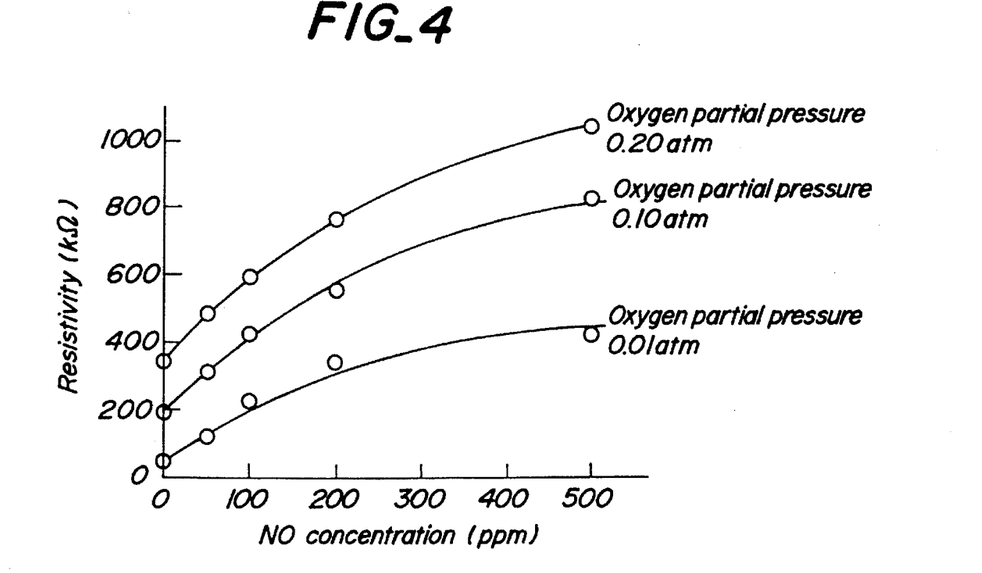
FIG. 4 is a graph showing one measured result of NO concentration by utilizing a measuring apparatus according to a comparative example in the case of using porous $TiO_2$ sintered body as an MOS.

Generally, the oxygen concentration of an exhaust gas discharged from an internal combustion engine or an exhaust gas discharged from a dust incinerator varies greatly. In these exhaust gases, we find that the resistance of the MOS varies greatly in response to a variation of an oxygen partial pressure in the exhaust gas as well as the specific gas concentration. Moreover, the detected resistance is influenced by both the specific gas concentration and the oxygen partial pressure. Therefore, it is not possible to detect a concentration of the specific gas component precisely. For example, as shown in FIG. 4 mentioned below, if the oxygen partial pressure is varied from 0.01 atm to 0.20 arm, resistivities of the MOS therebetween are largely different from each other while concentration of NO therebetween are identical with each other.

SUMMARY OF THE INVENTION

An object of the invention is to provide an apparatus and a method for measuring concentrations of specific gas components, in which a precise measurement can be performed even if an oxygen partial pressure is varied.

According to the invention, an apparatus for measuring a concentration of a specific gas component in an atmosphere comprises a measuring chamber for introducing the atmosphere; a gas diffusion resistant means for connecting the atmosphere with the measuring chamber; an MOS element arranged in the measuring chamber, the resistance of which varies corresponding to the concentration of a specific gas component; and an oxygen pump having a solid-electrolyte element with an oxygen ion transmitting property and a pair of electrodes arranged on both sides of the solid-electrolyte element, one electrode being communicated with an atmosphere in the measuring chamber. An oxygen partial pressure in the measuring chamber is controlled by the oxygen pump, and a resistance of the MOS element is measured under such a condition that the MOS element is exposed in the atmosphere, so that the concentration of the specific gas component is obtained from the resistance of the MOS.

According to the invention, a method for measuring a concentration of specific gas component in an atmosphere comprises the steps of introducing a gas to be measured into a measuring chamber through a gas diffusion resistant means, controlling an oxygen partial pressure in the measuring chamber to a predetermined level by means of an oxygen pump utilizing a solid-electrolyte element, measuring a resistance of an MOS element arranged in the measuring chamber, the resistance of which varies corresponding to a concentration of a specific gas component in the gas to be measured, and measuring a concentration of a specific gas component from the resistance of the MOS.

In accordance with the present invention, electrodes are arranged on both sides of a solid-electrolyte element made of zirconia so as to construct an oxygen pump, and one of the electrodes of the oxygen pump is arranged in a measuring chamber in which the MOS is arranged. Therefore, it is possible to control an oxygen partial pressure in the measuring chamber. Moreover, if a concentration of the specific gas component is measured in an atmosphere in which concentration of NO or the like and the oxygen partial pressure vary greatly, it is possible to measure the specific gas concentration such as NO or the like precisely with no timing delay i.e. on real time.

Therefore, according to the invention, when concentrations of poisonous gases such as NO or the like are measured in an atmosphere such as an exhaust gas of a combustion gas in which the oxygen partial pressure varies greatly, it is possible to realize a precise concentration measurement by utilizing an apparatus for measuring gas concentrations using the MOS. Accordingly, the importance of the present invention in the field of measuring apparatuses is very great.

DESCRIPTION OF THE PREFERRED EMBODIMENT

As an MOS element, use is made of an element made of an oxide such as $TiO_2$, $SnO_2$, $ZnO_2$, NiO, Fe—O, $WO_2$, $In_2O_3$, $Nb_2O_5$, $V_2O_5$, Mn—O, Cu—O, CoO or the like, or a solid solution or an oxide composite both including respective oxides mentioned above. In the MOS element, a ratio between metal ions and oxygen ions and a crystal structure are varied corresponding to a temperature and an oxygen partial pressure during an element producing step or an environmental condition to be used.

Moreover, the MOS element may be made of a porous body or a densified sintered body of an MOS, or an MOS film formed with or on a supporting body. Electrodes used for measuring a resistance are arranged on the MOS element and the MOS element with the electrodes is accommodated in a measuring chamber.

An apparatus using the MOS element can detect all the gas components except for oxygen, but it is preferably used for measuring specific gas components such as CO, $CO_2$, NO, $NO_2$, $NH_3$, $H_2$, $H_2O$, $SO_2$, HCl, or $H_2S$.

An oxygen pump is formed by a solid-electrolyte element made of zirconia having an oxygen ion conductivity on which a positive electrode and a negative electrode are arranged. In the oxygen pump, an oxygen component becomes an oxygen ion at the positive electrode, the oxygen ion is transmitted through the solid-electrolyte element, and the oxygen ion becomes the oxygen component at the negative electrode and is discharged. Therefore, the oxygen component is moved from a positive electrode side to a negative electrode side.

A shape of the solid-electrolyte element is not limited, but a thin plate is preferred. As an electrode, it is preferred to use a porous electrode. The porous electrode can be formed by printing a paste on the element and firing it.

Moreover, in order to increase a temperature of the MOS to a temperature preferable for measuring a gas concentration, or in order to increase a temperature of the oxygen pump to a temperature at which the oxygen pump is active, it is preferred to embed a heater of a resistance heating type or the like in a wall surface of a container consisting of the measuring chamber. Moreover, it is preferred to expose directly one electrode of the oxygen pump in the measuring chamber. However, if the electrode is not directly exposed in the measuring chamber, it is sufficient to communicate the electrode to an atmosphere in the measuring chamber through a predetermined passage.

According to the invention, a voltage applied between a pair of electrodes of the oxygen pump can be adjusted continuously. In this case, a ratio of the oxygen partial pressure between one electrode side of the oxygen pump can be adjusted continuously.

Moreover, the other electrode of a pair of electrodes of the oxygen pump is arranged in an atmosphere outside the measuring chamber, and a voltage supplied to the solid-electrolyte element is adjusted in such a manner that the positive electrode is positioned in the measuring chamber and the negative electrode is positioned outside the measuring chamber. In this case, an oxygen partial pressure in the measuring chamber can be controlled to a small level as compared with an oxygen partial pressure outside the measuring chamber. Therefore, if an oxygen partial pressure outside the measuring chamber is largely varied, a variation of an oxygen partial pressure in the measuring room can be made relatively small.

Further, the other electrode of a pair of electrodes of the oxygen pump is arranged in an atmosphere outside the measuring chamber, and a voltage applied to the solid-electrolyte element is adjusted in such a manner that the negative electrode is positioned in the measuring chamber and the positive electrode is positioned outside the measuring chamber. In this case, an oxygen partial pressure in the measuring chamber can be controlled to a large level as compared with an oxygen partial pressure outside the measuring chamber. Then, if the applied voltage is controlled to a sufficiently large level, it is possible to control an oxygen partial pressure in the measuring chamber always above a predetermined threshold level C. The construction mentioned above can be adopted if the resistance of the MOS element does not vary greatly in an oxygen partial pressure range above the threshold level C.

Moreover, an oxygen concentration reference chamber in which an oxygen concentration is maintained in a predetermined range can be provided, and the other electrode of a pair of electrodes of the oxygen pump is arranged in the oxygen concentration reference chamber. In this case, since an oxygen concentration in the oxygen concentration reference chamber is maintained at a constant level, it is possible to maintain an oxygen concentration in the measuring chamber at a constant level, if a voltage applied between a pair of electrodes of the oxygen pump is controlled at a constant level. Therefore, it is possible to control an oxygen concentration precisely in an easy manner.

Moreover, an oxygen partial pressure in the measuring chamber can be controlled in a predetermined range by arranging an oxygen sensor for measuring an oxygen concentration in the measuring chamber, and adding a signal obtained from the oxygen sensor to a voltage applied to the oxygen pump as a feedback. For example, if a signal obtained from the oxygen sensor is above a predetermined upper limit, a voltage applied to the oxygen pump is controlled in such a manner that the positive electrode is positioned in the measuring chamber. In this case, the oxygen component in the measuring chamber is discharged, and thus an oxygen partial pressure in the measuring chamber can be decreased. Moreover, if a signal obtained from the oxygen sensor is under a predetermined lower limit, a voltage applied to the oxygen pump is controlled in such a manner that the negative electrode is positioned in the measuring chamber. In this case, the oxygen component is supplied into the measuring chamber, and thus an oxygen partial pressure in the measuring chamber can be increased.

If the feedback control mentioned above is performed, it is possible to maintain an oxygen partial pressure in the measuring chamber at a predetermined range in an easy manner even when the oxygen concentration reference chamber is not provided and the other electrode of a pair of electrodes of the oxygen pump is exposed to an atmosphere outside the measuring chamber under the condition such that an oxygen concentration in the atmosphere varies greatly.

In the present invention, a gas diffusion resistant means is arranged in the measuring chamber. This gas diffusion resistant means functions to supply or discharge an atmospheric gas into or out of the measuring chamber. The number of the gas diffusion resistant means is not limited to one, since a plurality of the gas diffusion resistant means can be used.

Figure 1:
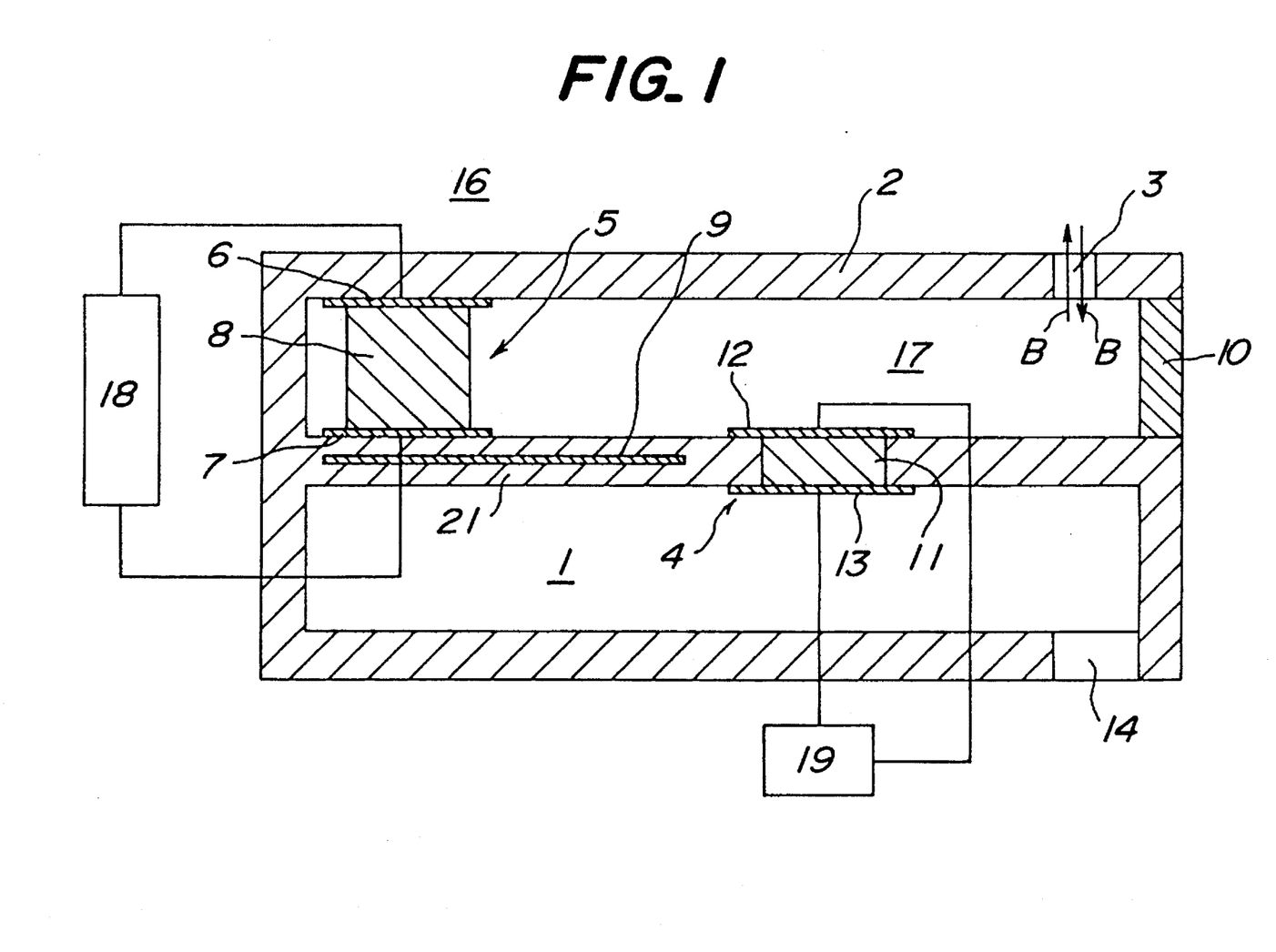
FIG. 1 is a cross sectional view showing one embodiment of an apparatus for measuring a gas concentration according to the invention.

Hereinafter, the present invention will be explained in detail with reference to the drawings. FIG. 1 shows an apparatus for measuring a gas concentration with an oxygen concentration reference chamber. In FIG. 1, a measuring chamber 17 is formed in a container 2, and a hole 3 is arranged in the container 2 as a gas diffusion resistant means. An atmospheric gas in an outer atmosphere 16 outside the measuring chamber 17 is supplied or discharged through the hole 3 as shown by arrows B.

Respective electrodes 6 an 7 are arranged on both sides of an MOS element 8 so as to form a measuring element 5 for measuring a concentration of a specific gas component. The measuring element 5 is arranged in the measuring chamber 17, and an opening of the container 2 is plugged by a fused member 10. The electrodes 6 and 7 are connected respectively to a controller 18 having a known construction.

An oxygen concentration reference chamber 1 is arranged under the measuring chamber 17, and a reference gas is introduced into the oxygen concentration reference chamber 1 through a hole 14. A solid-electrolyte element 11 is arranged in a partition 21, and electrodes 12 and 13 are respectively arranged on both sides of the solid-electrolyte element 11 so as to form an oxygen pump 4. The electrode 12 is exposed to the measuring chamber 17, and the electrode 13 is exposed to the oxygen concentration reference chamber 1. The electrodes 12 and 13 are connected respectively to a controller 19. Moreover, a heater 9 is embedded in the partition 21.

Figure 2:
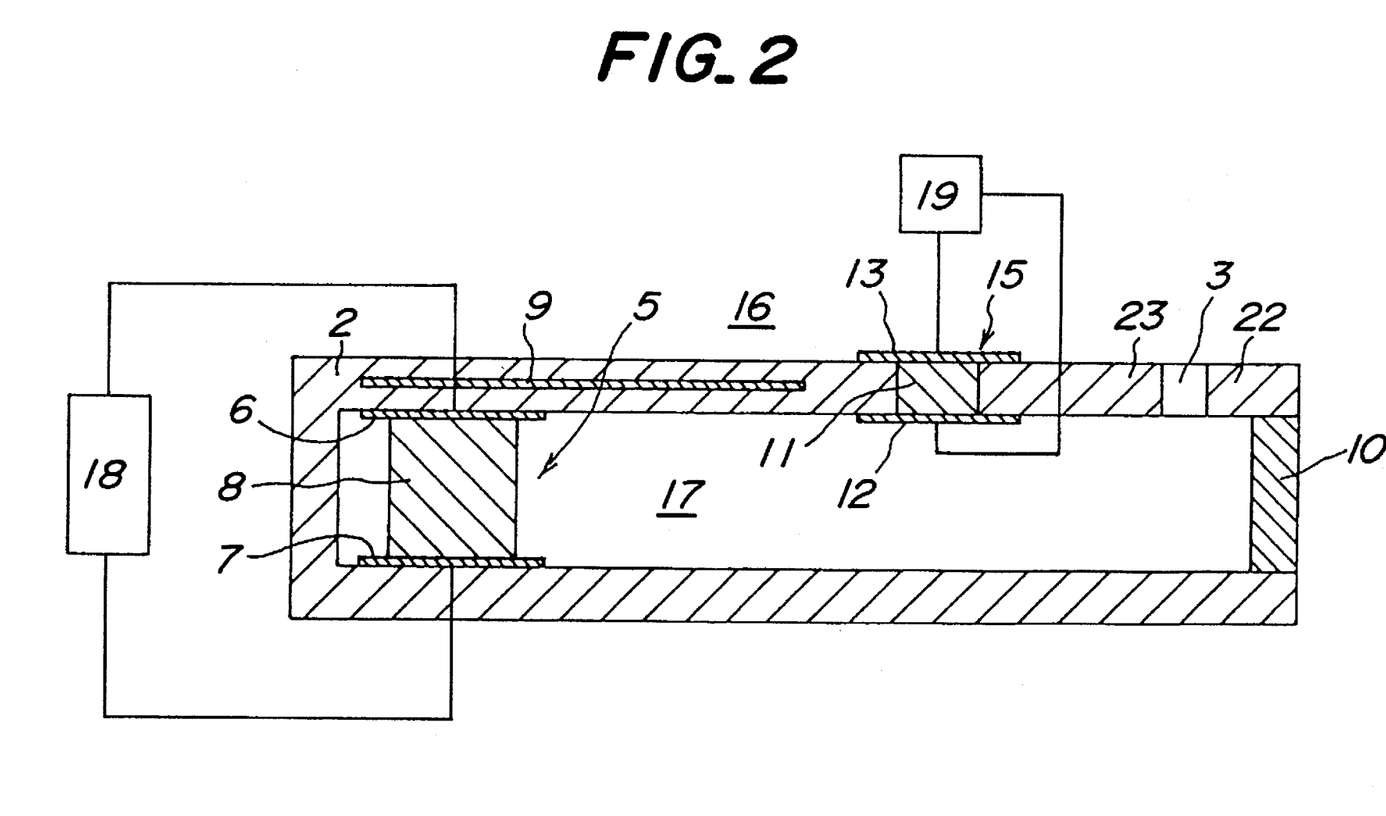
FIG. 2 is a cross sectional view illustrating another embodiment of the apparatus for measuring a gas concentration according to the invention.

In an apparatus for measuring a concentration of a specific gas component shown in FIG. 2, the measuring chamber 17 is formed in a container 22, and the hole 3 is arranged in a wall 23 of the container 22. The solid-electrolyte element 11 is arranged in the wall 23, and the electrodes 12 and 13 are arranged respectively on both sides of the wall 23 so as to form an oxygen pump 15. The electrode 12 is exposed to the measuring chamber 17 and the electrode 13 is exposed to the outer atmosphere 16. Moreover, the heater 9 is embedded in the container 22.

Figure 3:
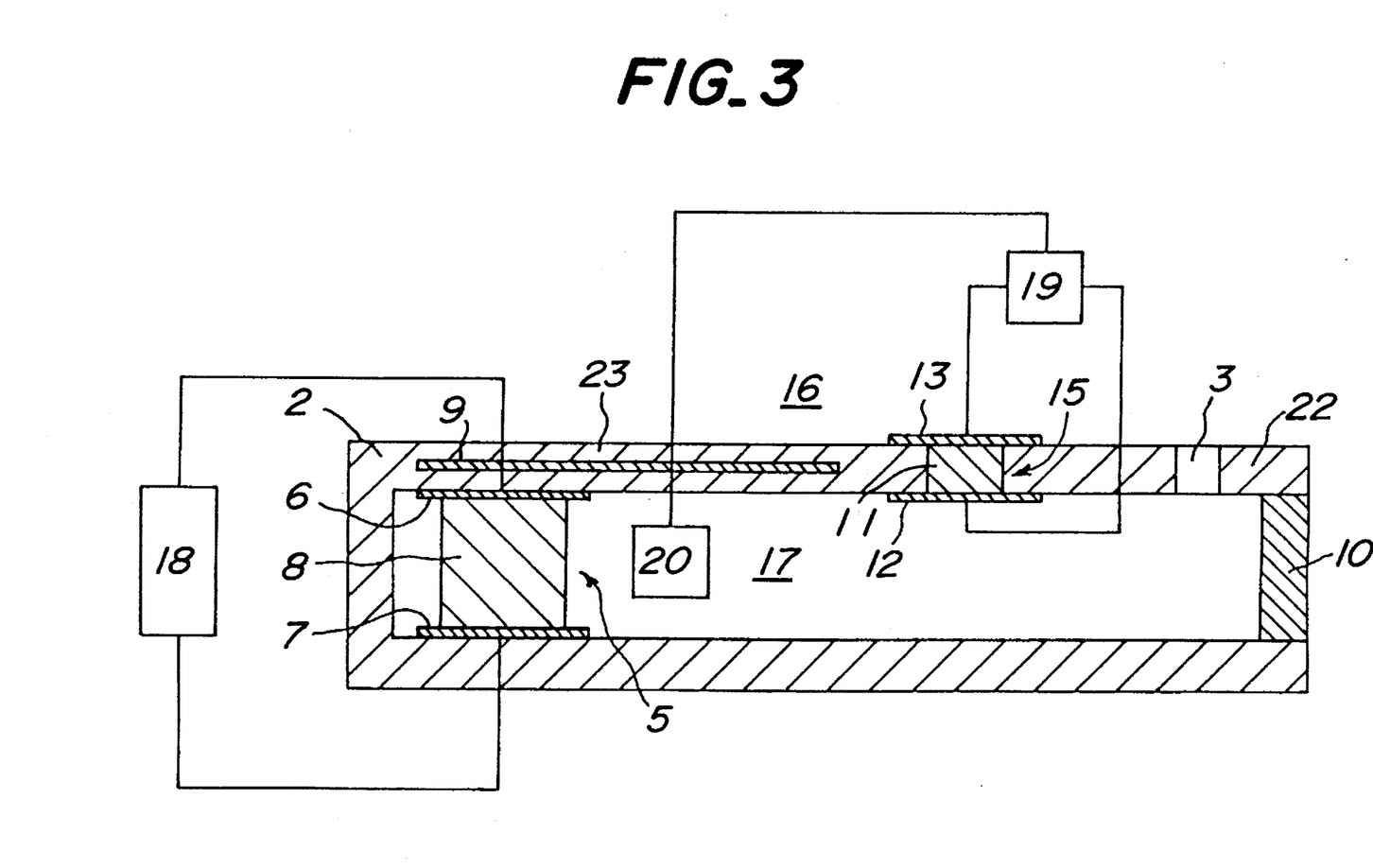
FIG. 3 is a cross sectional view depicting still another embodiment of the apparatus for measuring a gas concentration according to the invention.

In an apparatus for measuring a concentration of a specific gas component shown in FIG. 3, the measuring chamber 17 is formed in the container 22, and the hole 3 is arranged in the wall 23 of the container 22. The solid-electrolyte element 11 is arranged in the wall 23, and the electrodes 12 and 13 are arranged respectively on both sides of the wall 23 so as to form the oxygen pump 15. The electrode 12 is exposed to the measuring chamber 17 and the electrode 13 is exposed to the outer atmosphere 16. Moreover, the heater 9 is embedded in the container 22.

In the embodiment shown in FIG. 3, an oxygen sensor 20 is arranged in the measuring chamber 17, and is connected to the controller 19. Then, if a signal obtained from the oxygen sensor 20 is above a predetermined upper limit, a voltage applied to the oxygen pump 15 is controlled in such a manner that the electrode 12 in the measuring chamber 17 is positively charged. If a signal obtained from the oxygen sensor 20 is under a predetermined lower limit, a voltage applied to the oxygen pump 15 is controlled in such a manner that the electrode 12 in the measuring chamber 17 is negatively charged.

Hereinafter, actual experimental results will be explained.

Experiment 1

The apparatus for measuring a concentration of a specific gas component having a construction shown in FIG. 1 was prepared. As the container 2, use was made of an air-tight sintered body made of zirconia having the hole 3. Then, a slurry including $TiO_2$ particles having a particle size of about 0.5 μm was supplied in the container 2, and the slurry was dried and sintered so as to obtain the MOS element 8 made of a porous $TiO_2$ sintered body. Then, the opening portion of the container 2 through which the slurry was introduced was plugged by the fused member 10. As the solid-electrolyte element 11, use was made of zirconia.

As a comparative example, an apparatus for measuring a concentration of a specific gas component, having the same construction shown in FIG. 1 except that no oxygen pump 4 was arranged, was prepared. The other construction and the material to be used were the same as those of the apparatus for measuring a concentration of a specific gas according to the invention.

At first, a measuring experiment was performed with respect to the apparatus according to the comparative example. A temperature at which the experiment was performed was 600° C., and a concentration of NO in the outer atmosphere was varied in a range of 0–500 ppm as shown in FIG. 4. Moreover, an oxygen partial pressure was also varied at 0.01 atm, 0.10 atm and 0.20 atm as shown in FIG. 4. A total pressure of the outer atmosphere was 1 atm. Measuring results of resistivities of the MOS element were also shown in FIG. 4 respectively.

As can be understood from FIG. 4, if the oxygen partial pressure is varied, the resistance of the MOS element is varied extremely. Under such a condition, if the oxygen partial pressure varies greatly, it is impossible to measure the NO concentration. Moreover, even if a variation of the oxygen partial pressure is small, it is difficult to detect the resistance accurately.

Figure 5:
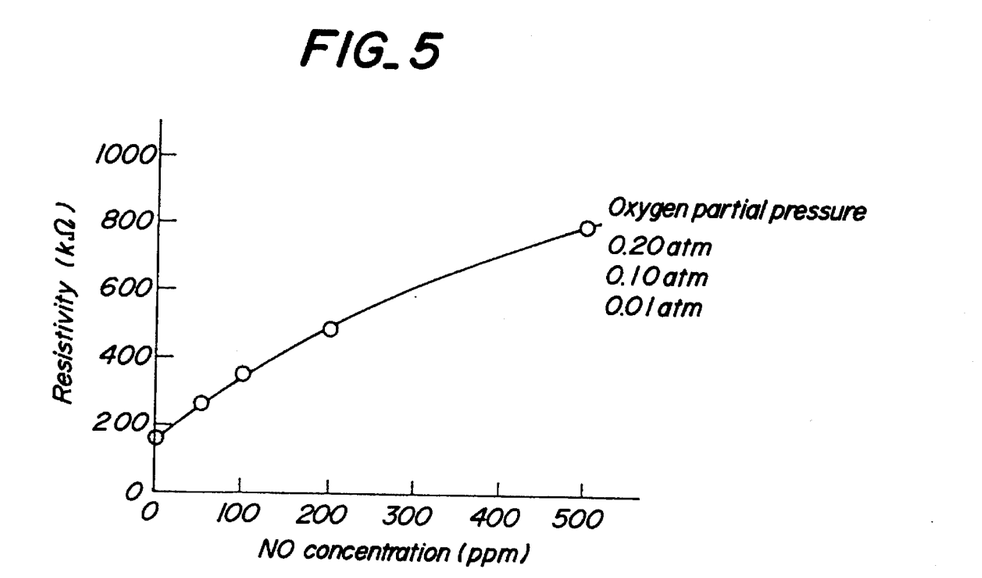
FIG. 5 is a graph illustrating one measured result of NO concentration by utilizing a measuring apparatus according to the present invention in the case of using porous $TiO_2$ sintered body as the MOS.

Then, a measuring experiment was performed with respect to the apparatus according to the invention. A temperature at which the experiment was performed was 600° C., and a concentration of NO in the outer atmosphere was varied in a range of 0–500 ppm as shown in FIG. 5. Moreover, an oxygen partial pressure was also varied at 0.01 atm, 0.10 atm and 0.20 atm as shown in FIG. 5. A total pressure of the outer atmosphere was 1 atm.

Further, the oxygen partial pressure in the oxygen concentration reference chamber 1 was set at 0.20 atm. Moreover, a voltage of 56 mV was applied between the electrodes 12 and 13 in such a manner that a ratio of the oxygen partial pressure between the electrode 13 side and the electrode 12 side was 20:1, so that the electrode 12 was positively charged. Measuring results of resistivities of the MOS element are also shown in FIG. 5 respectively.

Figure 6:
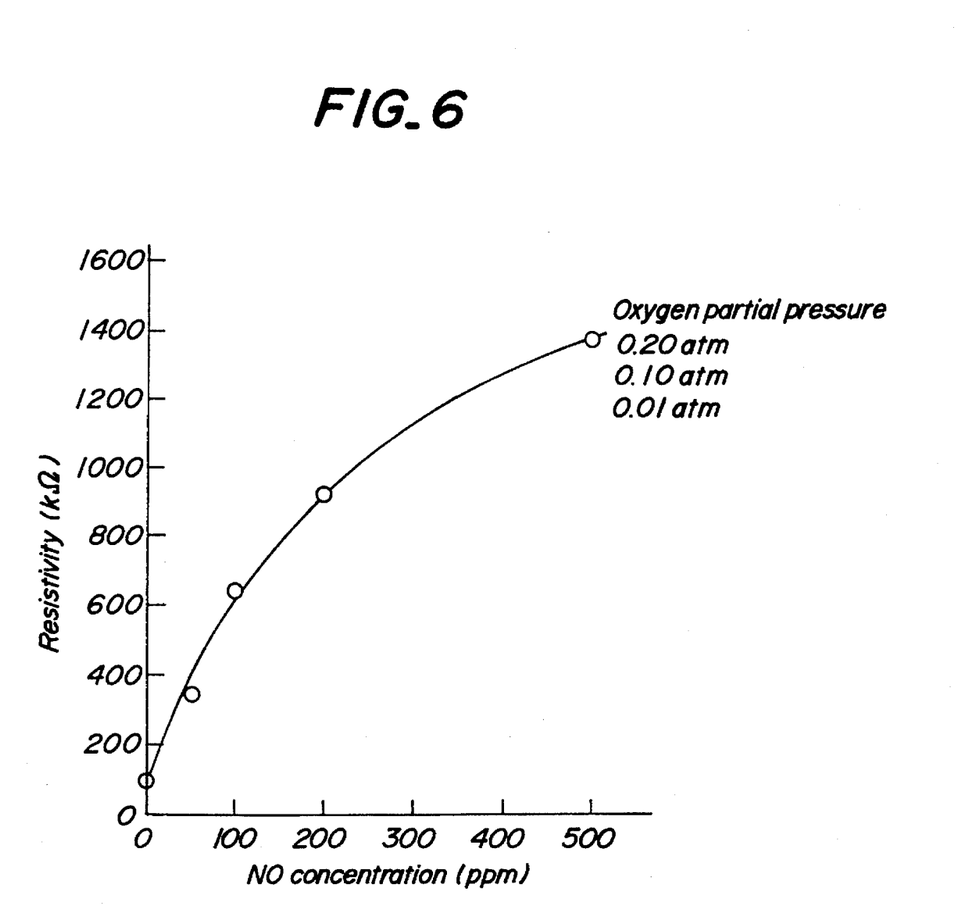
FIG. 6 is a graph depicting another measured result of NO concentration by utilizing a measuring apparatus according to the present invention in the case of using porous $TiO_2$ sintered body as the MOS.

Then, a voltage of 186 mV was applied between the electrodes 12 and 13 in such a manner that a ratio of the oxygen partial pressure between the electrode 13 side and the electrode 12 side was 20000:1, so that the electrode 12 was positively charged. Measuring results of resistivities of the MOS element are also shown in FIG. 6 respectively.

As can be understood from the results mentioned above, according to the invention, it is possible to measure the NO concentration accurately even if the oxygen partial pressure in the outer atmosphere varies greatly.

Experiment 2

The apparatus for measuring a concentration of a specific gas component according to the invention and the comparative example were prepared as is the same as the experiment 1, and a measuring experiment was performed with respect to the apparatuses. The difference was that the MOS element was made of a porous $WO_3$ sintered body.

Figure 7:
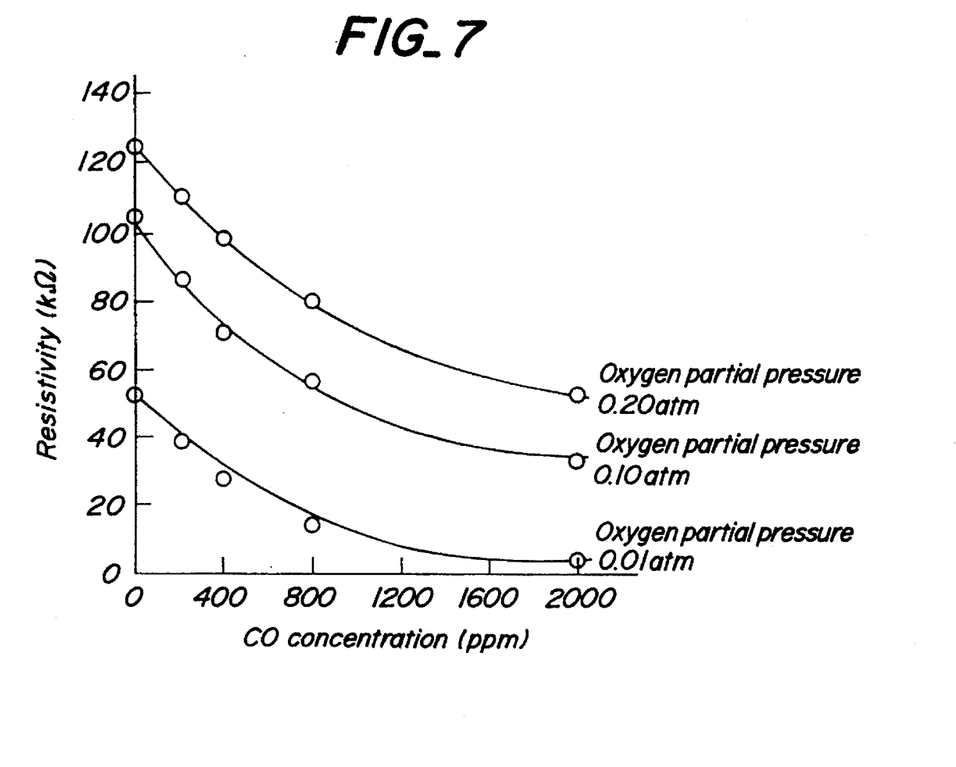
FIG. 7 is a graph showing one measured result of CO concentration by utilizing a measuring apparatus according to the comparative example in the case of using porous $WO_3$ sintered body as the MOS.

At first, a measuring experiment was performed with respect to the apparatus according to the comparative example. A temperature at which the experiment was performed was 400° C., and a concentration of CO in the outer atmosphere was varied in a range of 0~2000 ppm as shown in FIG. 7. Moreover, an oxygen partial pressure was also varied at 0.01 atm, 0.10 atm and 0.20 atm as shown in FIG. 7. A total pressure of the outer atmosphere was 1 atm. Measuring results of resistivities of the MOS element are also shown in FIG. 7 respectively.

As can be understood from FIG. 7, if the oxygen partial pressure is varied, the resistance of the MOS element is varied extremely. Under such a condition, if the oxygen partial pressure varies greatly, it is impossible to measure the CO concentration. Moreover, even if a variation of the oxygen partial pressure is small, it is difficult to detect the resistance accurately.

Figure 8:
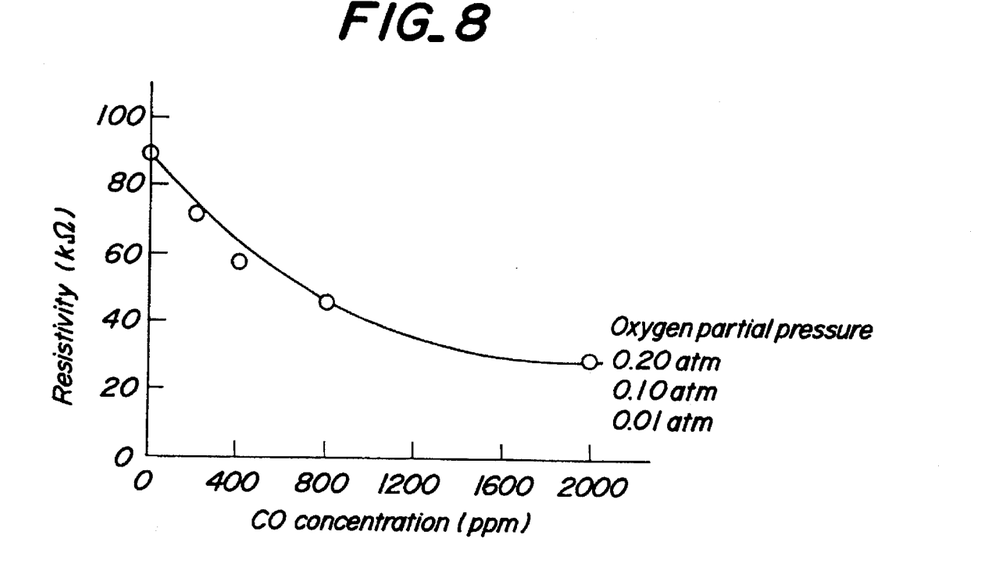
FIG. 8 is a graph illustrating one measured result of CO concentration by utilizing a measuring apparatus according to the present invention in the case of using porous $WO_3$ sintered body as the MOS.

Then, a measuring experiment was performed with respect to the apparatus according to the invention. A temperature at which the experiment was performed was 400° C., and a concentration of CO in the outer atmosphere was varied in a range of 0~2000 ppm as shown in FIG. 8. Moreover, an oxygen partial pressure was also varied at 0.01 atm, 0.10 atm and 0.20 atm as shown in FIG. 8. A total pressure of the outer atmosphere was 1 atm.

Further, the oxygen partial pressure in the oxygen concentration reference chamber 1 was set at 0.20 atm. Moreover, a voltage of 12 mV was applied between the electrodes 12 and 13 in such a manner that a ratio of the oxygen partial pressure between the electrode 13 side and the electrode 12 side was 2:1, so that the electrode 12 was positively charged. Measuring results of resistivities of the MOS element are also shown in FIG. 8 respectively.

As can be understood from the results mentioned above, according to the invention, it is possible to measure the NO concentration accurately even if the oxygen partial pressure in the outer atmosphere varies greatly. Therefore, according to the invention, it is possible to measure a concentration of a specific gas component even in an atmosphere in which oxygen concentration varies greatly. Moreover, it is possible to improve a resistance measuring accuracy.

As mentioned above, according to the invention, in the apparatus for measuring a concentration of a specific gas component, it is possible to detect the resistance accurately even if an oxygen partial pressure in an atmosphere or a gas flow to be measured varies greatly. Therefore, in the atmosphere in which the oxygen partial pressure is largely varied such as an exhaust gas or a firing gas, the apparatus for measuring a gas concentration utilizing an MOS element can be used for measuring a poisonous gas or a combustion gas in which the oxygen partial pressure varies greatly. Moreover, it is possible to perform an accurate measuring operation. Accordingly, the importance of the present invention in the field of measuring apparatuses is very large.

What is claimed is:

1. An apparatus for measuring a concentration of a specific gas component in an external atmosphere, comprising:

a measuring chamber for receiving a sampling of the external atmosphere;

gas diffusion resistance means for providing communication between said measuring chamber and the external atmosphere;

an oxygen pump for controlling the oxygen partial pressure of the atmosphere contained in said measuring chamber, said oxygen pump being arranged proximate said gas diffusion means and comprising (i) an ion conductive solid electrolyte element, (ii) a first electrode formed on one side of said ion conductive solid electrolyte element, and (iii) a second electrode formed on an opposite side of said ion conductive solid electrolyte element, one of said first and second electrodes being exposed to said measuring chamber; and a metal oxide semiconductor element arranged in said measuring chamber remote from said gas diffusion means relative to the position of said oxygen pump, wherein a measured resistance of said metal oxide semiconductor element represents the concentration of the specific gas component to be measured, regardless of changes in oxygen partial pressure of the external atmosphere.

2. The apparatus according to claim 1, further comprising an oxygen concentration reference chamber, in which an oxygen concentration is maintained constant, and one of said first and second electrodes is exposed to said oxygen concentration reference chamber, while the other one of said first and second electrodes is exposed to said measuring chamber.

3. The apparatus according to claim 2, wherein a voltage applied between said first and second electrodes is controlled at a constant level to within a predetermined range so as to control an oxygen partial pressure in said measuring chamber.

4. The apparatus according to claim 1, further comprising an oxygen sensor for measuring an oxygen concentration in said measuring chamber, and a signal obtained from said oxygen sensor is added to a voltage applied to said oxygen pump as feedback to control an oxygen partial pressure in said measuring chamber to within a predetermined range.

5. The apparatus according to claim 1, further comprising a heater for heating said measuring chamber.

6. A method for measuring a concentration of a specific gas component in an atmosphere, comprising the steps introducing a gas to be measured into a measuring chamber through gas diffusion resistance means;

controlling an oxygen partial pressure of the gas in the measuring chamber to a predetermined level by means of an ion conductive solid electrolyte oxygen pump arranged proximate the gas diffusion resistance means;

then exposing the gas to a metal oxide semiconductor element arranged in the measuring room remote from the gas diffusion resistance means; and measuring the resistance of the metal oxide semiconductor element to determine the concentration of the specific gas component to be measured.

* * * * *